United States Patent
Kelly (10) Patent No.: US 9,387,110 B2
(45) Date of Patent: Jul. 12, 2016

(54) VARIABLE TENSION GLOVE

(71) Applicant: The Kelly Clientele Group, LLC, Lynwood, IL (US)

(72) Inventor: Robert Kelly, Lynwood, IL (US)

(73) Assignee: The Kelly Clientele Group, LLC, Lynwood, IL (US)

( * ) Notice: Subject to any disclaimer, the term of this patent is extended or adjusted under 35 U.S.C. 154(b) by 141 days.

(21) Appl. No.: 14/198,545

(22) Filed: Mar. 5, 2014

(65) Prior Publication Data

US 2014/0257159 A1    Sep. 11, 2014

Related U.S. Application Data

(60) Provisional application No. 61/772,754, filed on Mar. 5, 2013.

(51) Int. Cl.
*A61F 5/00* (2006.01)
*A61F 5/01* (2006.01)

(52) U.S. Cl.
CPC ....... *A61F 5/0118* (2013.01); *A61F 2005/0179* (2013.01)

(58) Field of Classification Search
CPC ........... A61F 2005/0179; A61F 5/0118; A61F 5/013; A61N 1/36003; A61N 1/36014; A63C 17/267; A63C 17/0013; B62K 23/02; B62K 19/46; B62K 2202/00; B62M 23/02; B62M 6/10; B62M 7/08; B62M 6/00; B63H 7/02; B63H 7/00; B60K 8/00; B60R 2019/007; B60R 2021/0051; A43C 11/165; A43C 11/16; A43C 11/008; A43C 11/004; A43C 11/00; A43C 1/04; A43C 1/00; A43C 1/003; A43B 5/16; A43B 11/00; A43B 3/0005; A43B 5/1666; A43B 1/04; A43B 23/0245; A63B 21/0004; A63B 21/4019; A63B 23/16; A63B 21/00061; A63B 21/00069; A63B 21/023; A63B 21/0428; A63B 21/0442; A63B 21/055; A63B 21/0552; A63B 21/0555; A63B 21/4025

USPC ............. 602/20–22; 482/44, 47, 48, 121, 124

See application file for complete search history.

(56) References Cited

U.S. PATENT DOCUMENTS

| | | | |
|---|---|---|---|
| 3,347,547 A | 10/1967 | Hynes | |
| 4,602,620 A * | 7/1986 | Marx | A61F 5/10 602/21 |
| 5,447,490 A * | 9/1995 | Fula | A63B 21/0004 482/124 |
| 5,538,488 A * | 7/1996 | Villepigue | A63B 21/0004 482/44 |
| 5,697,103 A | 12/1997 | Wiggins | |
| 5,876,363 A * | 3/1999 | Marx | A61F 5/0118 601/40 |
| 7,731,633 B1 | 6/2010 | Williams | |
| 2003/0195093 A1 | 10/2003 | White | |
| 2010/0311546 A1 | 12/2010 | Kupferman | |

FOREIGN PATENT DOCUMENTS

GB    2237726 A    5/1991

* cited by examiner

*Primary Examiner* — Michael Brown
(74) *Attorney, Agent, or Firm* — Richards Patent Law, P.C.

(57) ABSTRACT

The present disclosure provides a variable tension rehabilitation glove including a glove body configured to receive a hand of a user, a wrist band surround the wrist portion, and a plurality of tension bands connecting distal portions of finger portions to a movable tension device for varying the tension of the tension bands.

18 Claims, 11 Drawing Sheets

VARIABLE TENSION GLOVE

CROSS-REFERENCE TO RELATED APPLICATIONS

This application incorporates by reference and claims priority to U.S. Provisional Application 61/772,754 filed on Mar. 5, 2013.

BACKGROUND OF THE INVENTION

The present subject matter relates generally to a variable tension rehabilitation glove that may be worn during normal activity and sports activity.

Rehabilitation from a hand injury involves the strengthening of muscles which may have atrophied during the healing process. Typically, rehabilitation includes strengthening of the hand muscles through resistance training. For example, resistant bands, stress balls, and other items may be used to strengthen the muscles in the fingers and palm, as well as the dorsal side of the hand.

Current rehabilitation methods include the use of various devices involving complicated systems of tension bands that may be cumbersome to arrange on a users hand. Even in examples in which the rehabilitation apparatus is in the form of a glove, the user may only use the glove during rehabilitation, due to the cumbersome nature of the design of the glove. For example, the rehabilitation glove may be bulky such that the user may not comfortably wear the glove to strengthen his or her hand during normal daily activity or during sports activities.

Further, many conventional systems only offer one degree of tension within the rehabilitation device. However, a user may need less tension during the beginning weeks of rehabilitation and more tension during the subsequent weeks of physical therapy. In order to provide a user with a gradient of tensions, a physician may need to switch among a couple of different rehabilitation devices to provide an increase in tension over time as the user strengthens his hand.

Not only do a majority of convention rehabilitation devices only provide one degree of tension during flexion or extension of the hand, but every finger has the same degree of tension as well. In other words, a user is not able to adjust the tension for individual fingers. For example, a user that has injured his middle finger may need less tension applied to the middle finger while the user needs more tension applied to the ring finger, which may have a lesser degree of injury.

In addition, current rehabilitation devices are designed to strengthen either the muscles used to close the hand into a first (flexion) or the muscles used to open a hand from a first (extension). In other words, the current systems only allow a user to strengthen the muscles used during flexion or extension of a user's hand, but not both. A user would need to use two separate devices to strengthen both the palmer muscles and dorsal muscles of a hand.

Accordingly, there is a need for a less bulky rehabilitation glove that strengthens both the muscles in the palmer and dorsal surfaces.

BRIEF SUMMARY OF THE INVENTION

The present disclosure provides various examples of a variable tension device that may be worn by a user during both normal activity and during sports activity.

The variable tension glove provided herein provides tension to a user's hand upon flexion and/or extension. The user has the ability to control and adjust the amount of the tension in the glove to customize the degree of tension within the rehabilitation exercises. In an example, a user may vary the tension in each finger individually, thus allowing for different tensions to be applied to individual fingers. In yet another example, the resistance provided by the glove is reversible such that the user may use the glove to rehabilitate the muscles used during both flexion and extension of the fingers of the hand.

In an embodiment, the variable tension rehabilitation glove includes a glove body comprising a palm portion, five finger portions, and a wrist portion including a wrist opening configured to receive a hand of a user, wherein the glove body includes a palmer surface and a dorsal surface. The glove includes a wrist band surrounding at least a portion of the wrist portion. In an example, the wrist band includes two operative ends configured to releasably attach to each other. The glove also includes a plurality of tension bands each including a first end and a second end, wherein the first end is connected to a distal end of the finger portions and the second end is attached to a movable tension device for varying the tension of the tension bands. The movable tension device is connected to the wrist band.

The glove may be convertible between a first position and a second position. When the glove is in the first position, the tension bands extend along the palmer surface of the finger portions and the movable tension device is adjacent to the palmer surface of the palm portion. When the glove is in the second position, the tension bands extend along the dorsal surface of the finger portions and the movable tension device is adjacent to the dorsal surface of the palm portion.

In an example, the movable tension device includes a longitudinal base plate and a connector plate engaged to slide along at least a portion of the length of the longitudinal base place, wherein the second ends of the tension bands connect to the connector plate, wherein the connector plate may temporarily lock into a plurality of positions along the length of the longitudinal base place, wherein the position of the connector plate relative to the longitudinal base plate effects the tension in the tension bands.

When the glove is in the first position, the longitudinal base plate may be adjacent to the palmer side of the glove body, and when the glove is in the second position, the longitudinal base plate is adjacent to the dorsal side of the glove body.

In another example, the wrist band includes an inner surface and an outer surface, wherein, when the glove is in the first position, the inner surface of the wrist band is adjacent to a wrist of a user, and when the glove is in the second position, the outer surface of the wrist band is adjacent to a wrist of a user.

The distal ends of the finger portions may include molded caps including finger tip anchorings, wherein the first end of the tension band attaches to the finger tip anchoring. The first end of the tension bands may include a band opening and the distal ends of the finger portions include a hook, wherein the band opening engages with the hook. The finger portions may include a molded band guide that includes a groove to receive the tension band.

The movable tension device may include a spring-loaded button configured to adjust the tension in the tension bands. Alternatively, the movable tension device may include an adjustment knob, wherein rotation of the adjustment knob effects the tension in the tension bands.

The movable tension device may include a connector plate connected to a rod including a plurality of rod openings. In such example, the wrist band includes a spring-loaded pin connected to a housing, wherein the housing receives at least a portion of the rod. The spring-loaded pin may be movable between the plurality of openings in the rod to alter the tension in the tension bands.

The glove may include a cover attached to the glove body, wherein the cover conceals the tension bands between the glove body and the cover.

In another embodiment, the glove includes a glove body comprising a palm portion, five finger portions, and a wrist portion including an opening configured to receive a hand of a user, wherein the glove body includes a palmer surface and a dorsal surface, and a wrist band surrounding at least a portion of the wrist portion. The glove also includes a plurality of tension bands each including a first end and a second end, wherein the first end is connected to a distal end of the finger portions and the second end is attached to a movable tension device for varying the tension of the tension bands, wherein the movable tension device is connected to the wrist band. The glove further includes a cover attached to the glove body, wherein the cover conceals the tension bands between the glove body and the cover.

The movable tension device may include a plurality of connectors attached to the wrist portion, wherein the second ends of the tension bands removably attach to the connectors. In an example, the movable tension device may include a set of at least two connectors, wherein each tension band corresponds to a set of at least two connectors, wherein the second end of the tension band is removably attached to the at least two connectors. The connectors within each set may be aligned proximal and distal to each other. The wrist band may cover at least a portion of the movable tension device.

An advantage of the present is providing a rehabilitation glove that may be worn while the user engages in daily activities and sports activities. For example, the glove may fit within other sporting gloves, such as a baseball glove or may be used while batting in baseball, golfing, playing football, playing hockey, playing soccer, performing mix martial arts (e.g., may be incorporated into the gloves), etc.

A further advantage of the present glove is that it allows the user to adjust the tension of the tension bands. In certain embodiments, the tension in the tension bands may be adjusted individually, thus, allowing different tensions among the fingers.

Another advantage of the present glove is that it is convertible and allows a user to strengthen both the dorsal and palmer sides of the same hand.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Figure 1A:
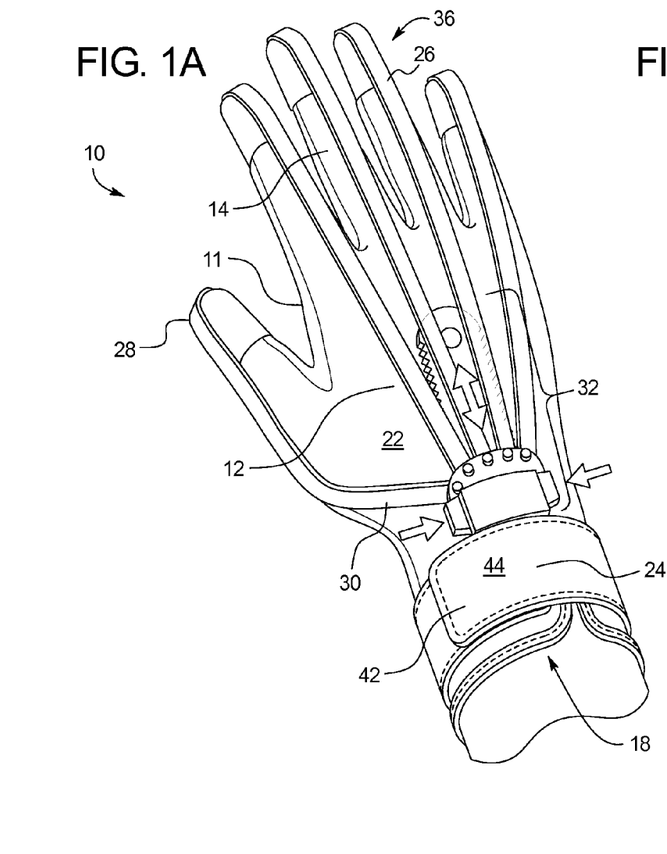
FIG. 1A is a perspective view of an embodiment of the glove disclosed herein in the second position.
Figure 1B:
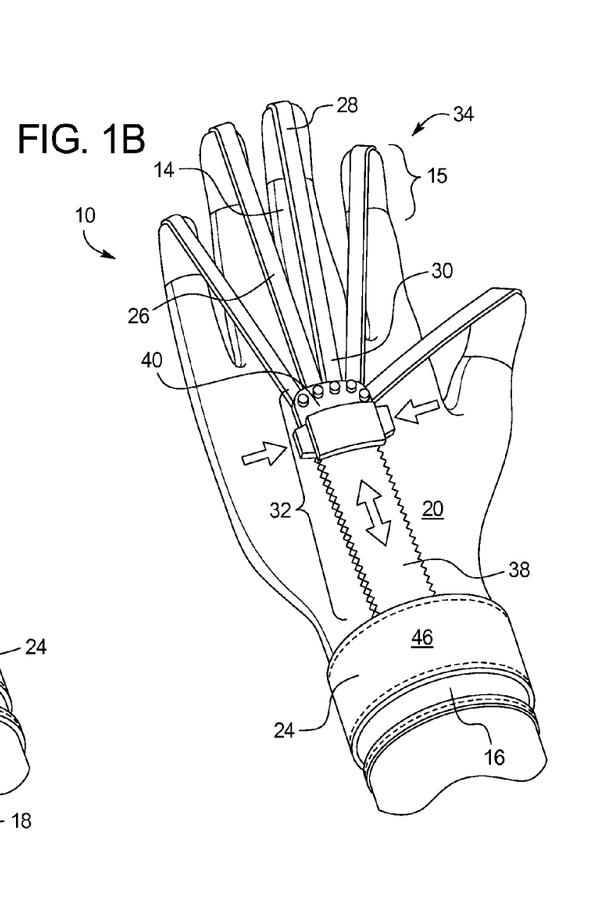
FIG. 1B is a perspective view of an embodiment of the glove disclosed herein in the first position.

As shown in FIGS. 1A-1B, the present disclosure provides a variable tension rehabilitation glove 10 including a glove body 11 comprising a palm portion 12, five finger portions 14, and a wrist portion 16 including a wrist opening 18 configured to receive a hand of a user. The glove body 11 also includes a palmer surface 20 and a dorsal surface 22. The glove body 11 may be made of any suitable material including, but not limited to, fabric, neoprene, plastic, metal, rubber, Teflon®, and combinations thereof. Preferably, the glove body 11 is made of a material that is flexible enough to comfortably bend during flexion and extension of a user's hand.

Figures 4A, 4B, 4C:
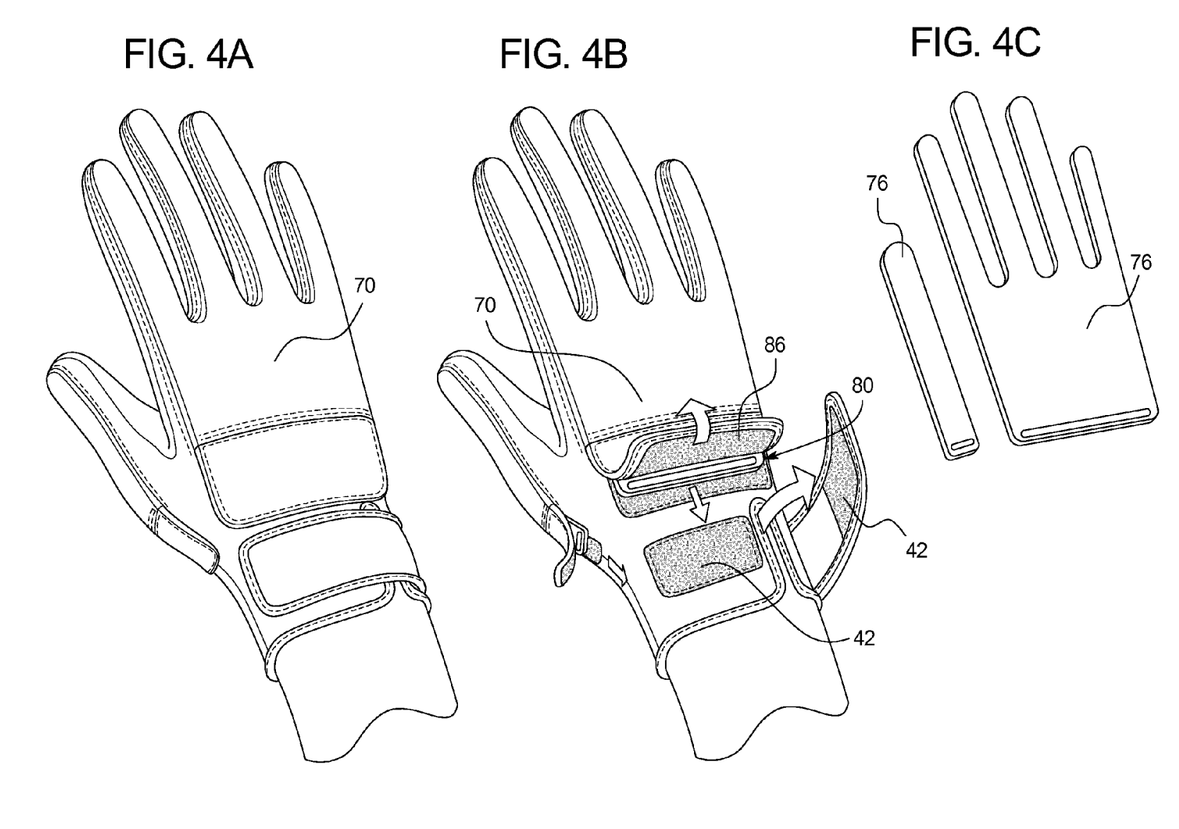
FIGS. 4A-4C are perspective views of another example of a glove including a rigid insert beneath a cover.

The glove 10 includes a wrist band 24 surrounding at least a portion of the wrist portion 16. The wrist band 24 may be integrally formed as part of the wrist portion, wherein the material of the wrist band 24 is an extension of the material of the wrist portion 16. In such example, the wrist band 24 may include one operative end 42 that is configured to attach to an outer surface of the wrist portion 16, as shown in FIGS. 4A-4B. Alternatively, the wrist band 24 may be distinct and separate from the wrist portion 16, wherein the wrist band 24 wraps around the wrist portion 16 to secure the glove 10 to a user's hand. In such example, the wrist band 24 includes two operative ends 42 configured to releasably attach to each other, as shown in FIGS. 1A-1B.

The glove 10 also includes a plurality of tension bands 26 each including a first end 28 and a second end 30. The tension bands 26 may be made of any suitable material. For example, the tension bands 26 may include elastic, rubber, leather, fabric, plastic, and combinations thereof. The tension bands 26 may be flat wherein a cross section of the tension bands 26 may be rectangular. Alternatively, the tension bands 26 may be round cables, wherein the cross section of the tension bands 26 may be circular.

In an example, the first end 28 of the tension bands 26 is connected to a distal portion 15 of the finger portions 14 and the second end 30 is attached to a movable tension device 32 for varying the tension of the tension bands 26, as shown in FIGS. 1A-1B. The first end 28 of the tension bands 26 may attach to the finger portions by any suitable method or mechanism. For example, the first ends 28 may be sewn, glued, fastened, locked, or otherwise temporarily or permanently attached to the distal portions 15 of the finger portions 14.

In certain embodiments, the distal portions 15 of the finger portions 14 may include molded caps 52 including a finger tip anchorings 54, wherein the first end 28 of the tension band 26 attaches to the finger tip anchoring 54. The tension bands 26 may screw or snap into the finger tip anchorings 54. The molded caps 52 may be made of a more rigid material that that of the glove body 11. For example, the glove body 11 may include neoprene while the molded caps 52 may include plastic or rubber.

Figure 2:
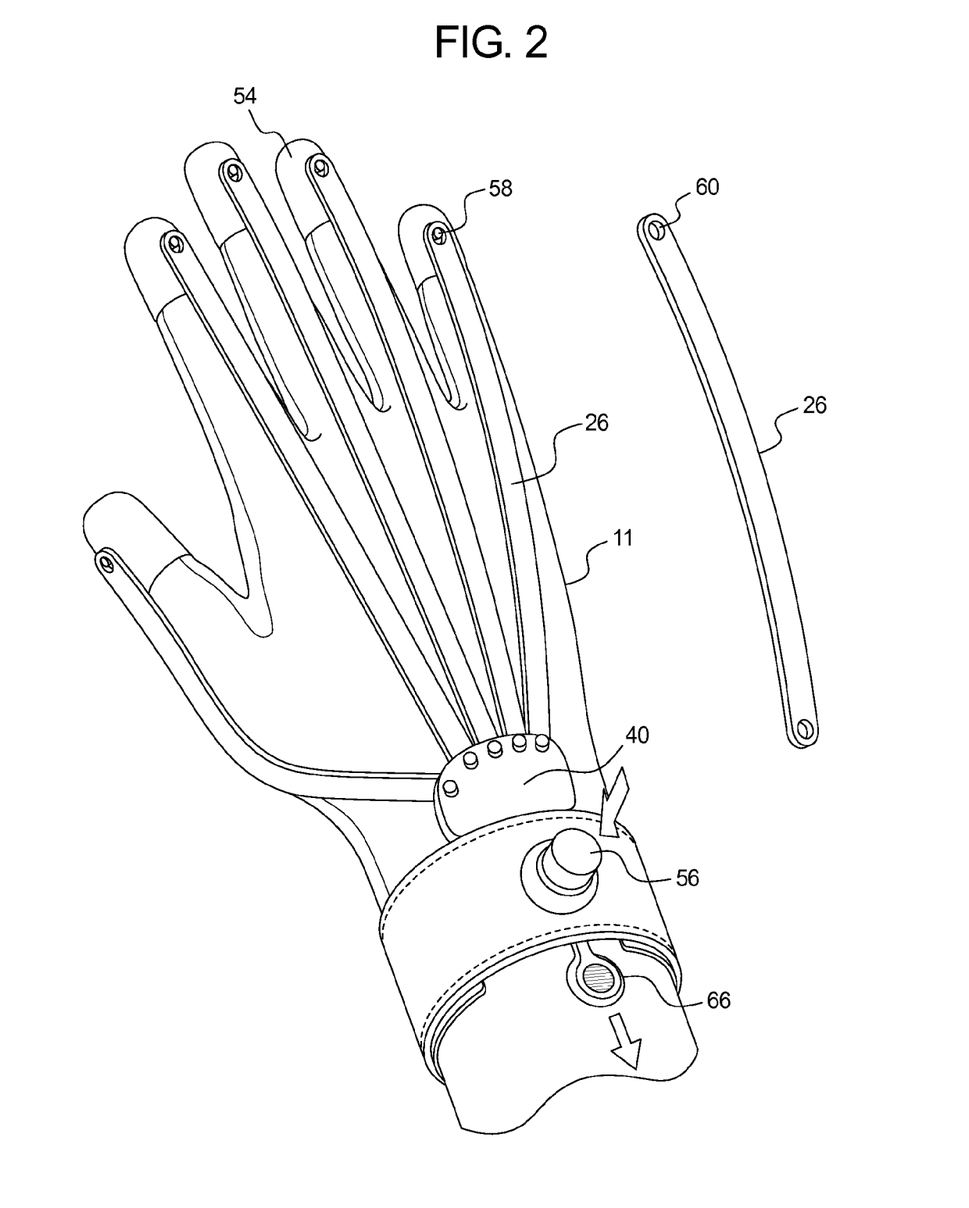
FIG. 2 is a perspective view of an embodiment of the glove including tension bands including band openings that attach to hooks on the on the distal ends of the finger portions.

FIG. 2 depicts another example of a method of attachment of the first end 28 to the distal portions 15 of the finger portions 14. As shown, the first end 28 of the tension bands 26 may include a band opening 60 and the distal portions 15 of the finger portions 14 may include a hook 58. The band opening 60 may removably engage with the hook 58 to connect the tension bands 26 to the distal portions 15.

Figure 3:
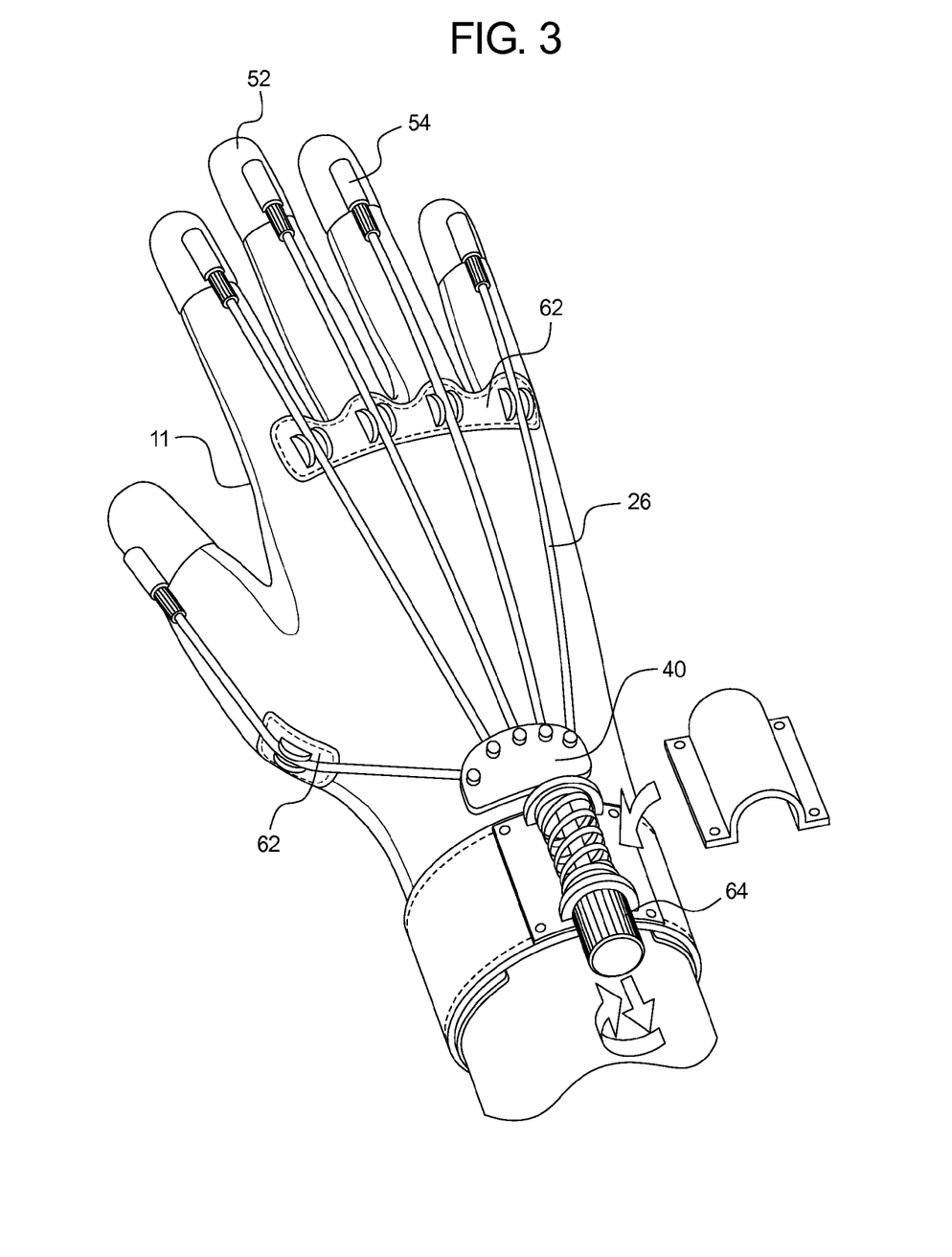
FIG. 3 is a perspective view of an example of a glove including a molded guide to receive the tension bands.

As shown in FIG. 3, the finger portions 14 may include a molded guide 62 that includes a groove 82 to receive the tension band 26. The molded guide 62 may be positioned adjacent to a user's knuckles such that the molded guide 62 maintains the proper alignment of the tension bands 26 when the glove 10 is in use. The molded guide 62 may also include a portion positioned near a thumb joint, as shown in FIG. 3.

As discussed above, the first end 28 of the tension bands 26 are attached to the movable tension device 32. The movable tension device 32 may be any suitable apparatus that is capable of varying the tension applied to the distal portions 15 of the finger portions 14 by way of the tension bands 26. The movable tension device 32 may be connected to the wrist band 24, and in other examples discussed below, the movable tension device 32 may be integrally formed with the wrist band 24 or wrist portion 16.

As shown in FIGS. 1A-1B, the movable tension device 32 may include a longitudinal base plate 38 and a connector plate 40, wherein the second ends 30 of the tension bands 26 connect to the connector plate 40. The second ends 30 may connect to the connector plate 40 by any suitable means. For example, the second ends 30 may be sewn, glued, fastened, locked, or otherwise temporarily or permanently attached to the connector plate 40. For example, the second ends 30 may include band openings 60 that attach to pins or hooks on the connector plate 40.

The connector plate 40 may be engaged to slide along at least a portion of the length of the longitudinal base place 38 such that the connector plate 40 may temporarily lock into a plurality of positions along the length of the longitudinal base place 38. The position of the connector plate 40 relative to the longitudinal base plate 38 effects the tension in the tension bands 26. For example, as the connector plate 40 is moved proximal, towards a user's wrist, more tension is applied to the tension bands 26. As the connector plate is moved distal, toward a user's fingers, less tension is applied to the tension bands 26.

Figure 6A:
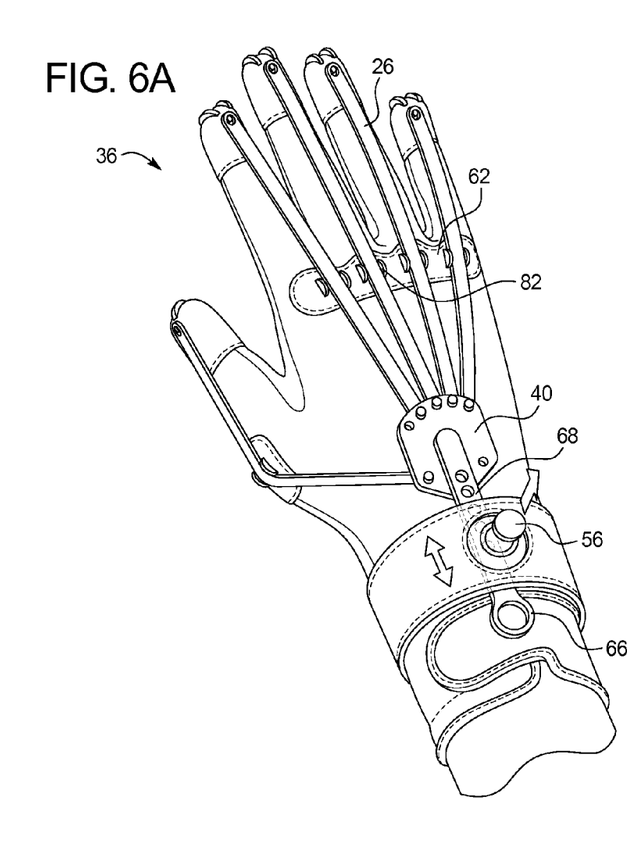
FIG. 6A is a perspective view of an embodiment of the glove in the second position including a movable tension device that includes a spring-loaded button and a rod having a plurality of rod openings to vary the tension in the tension bands.
Figure 6B:
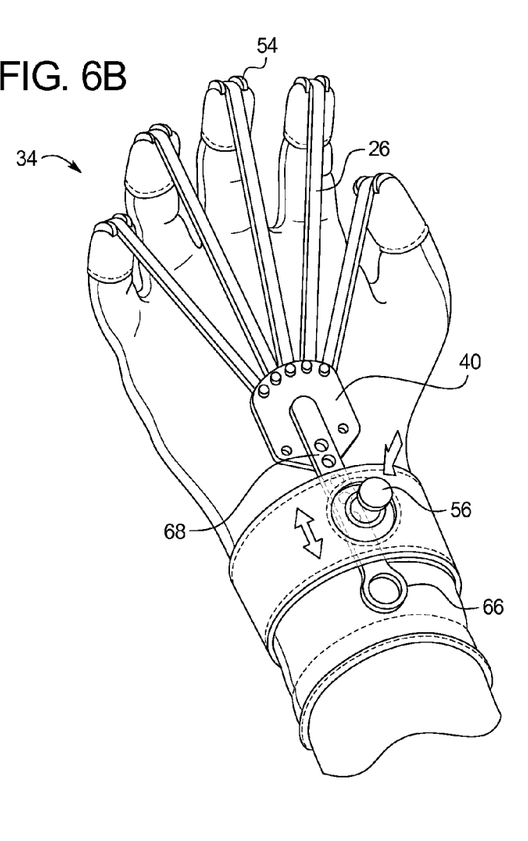
FIG. 6B is a perspective view of an embodiment of the glove in the first position including a movable tension device that includes a spring-loaded button and a rod having a plurality of rod openings to vary the tension in the tension bands.

Alternatively, or in addition to, the movable tension device 32 may include a spring-loaded button 56 configured to adjust the tension in the tension bands 26, as shown in FIG. 6A-6B. For example, the movable tension device 32 may include a connector plate 40 connected to a rod 66 including a plurality of rod openings 68. In such example, the movable tension device 32 includes a spring-loaded button 56, wherein the spring-loaded button 56 includes a pin that may be movable between the plurality of rod openings 68 in the rod 66 to alter the tension in the tension bands 26.

Figure 7A:
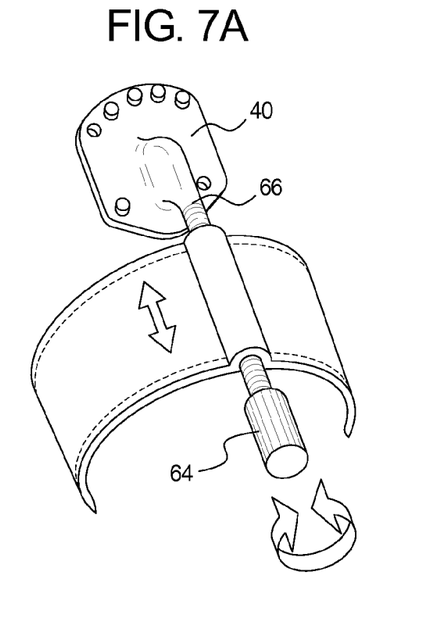
FIGS. 7A-7D are perspective views of various movable tension devices disclosed herein.
Figure 7B:
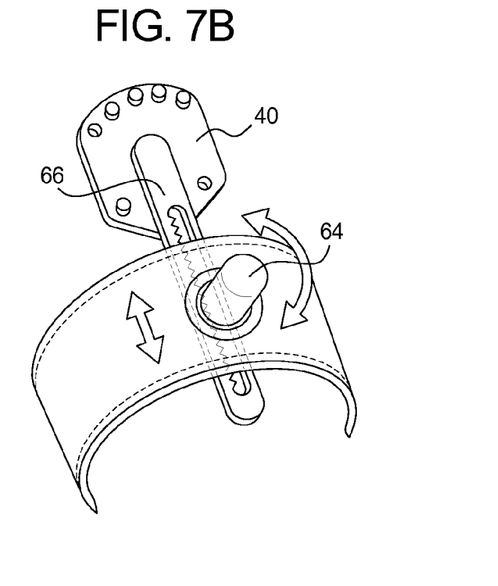
Figure 7C:
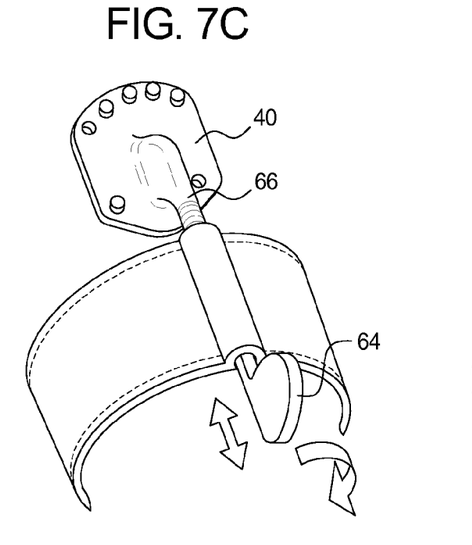
Figure 7D:
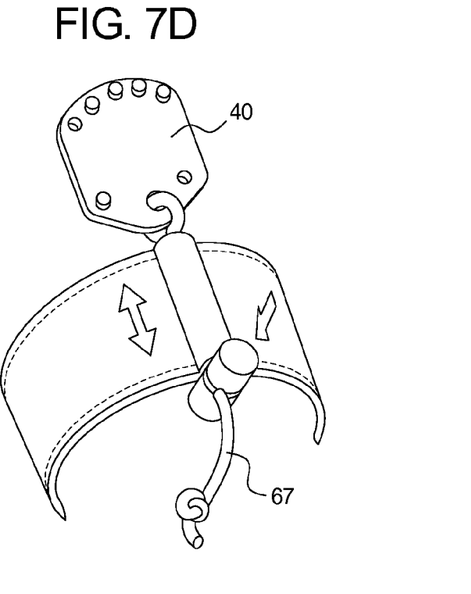

FIGS. 7A-7D depict various embodiments of the movable tension device 32. For example, as shown in FIG. 3 and FIGS. 7A-7C, the movable tension device 32 may include an adjustment knob 64, wherein rotation of the adjustment knob 64 effects the tension in the tension bands 26. FIG. 7D includes a movable tension device 32 wherein a pull string 67 is used to vary the tension in the tension bands 26 connected to the connector plate 40.

In an embodiment, the glove 10 is convertible between a first position 34 and a second position 36, as shown in FIGS. 1A-1B. The first position 34 may be used to rehabilitate hand muscles used during extension, and the second position 36 may be used to rehabilitation muscles used during flexion of a user's hand. When the glove is in the first position 34, the tension bands 26 extend along the palmer surface 20 of the finger portions 14 and the movable tension device 32 is adjacent to the palmer surface 20 of the palm portion 12, as shown in FIG. 1B. When the glove is in the second position 36, the tension bands 26 extend along the dorsal surface 22 of the finger portions 14 and the movable tension device 32 is adjacent to the dorsal surface 22 of the palm portion 12, as shown in FIG. 1A.

Typically, the movable tension device 32 may be moved from a position adjacent to the palmer surface 20 of the glove body 11 in the first position 34 to a position adjacent to the dorsal surface 22 in the second position 36. For example, when the movable tension device 32 includes the longitudinal base plate 38 and the connector plate 40, the longitudinal base plate 38 may be adjacent to the palmer surface 20 of the glove body in the first position 34. Alternatively, when the glove 10 is in the second position 36, the longitudinal base plate 38 is adjacent to the dorsal surface 22 of the glove body 11.

In an embodiment, the glove 10 may be converted between the first position 34 and the second position 36 by any suitable mechanism. For example, if the glove 10 is in the first position 34, the wrist band 24 may be unconnected and the movable tension device 32, now only connected to the glove body 11 through the attachment of the tension bands 26 to the finger portions 14, may be moved to the dorsal surface 22, wherein the wrist band 24 may be reattached forming the second position 36. In an example, a different surface of the wrist band is adjacent to a user's wrist in the second position 36 than in the first position 34. In other words, the point of rotation from the first position 34 to the second position 36 is the distal ends 15 of the finger portions 14. The wrist band 24 may include an inner surface 44 and an outer surface 46, wherein, when the glove 10 is in the first position 34, the inner surface 44 of the wrist band 24 is adjacent to a wrist of a user, and when the glove 10 is in the second position 36, the outer surface 46 of the wrist band 24 is adjacent to a wrist of a user.

Alternatively, the inner surface 44 of the wrist band 24 may be adjacent to a wrist of the user in both the first position 34 and the second position 36. For example, the wrist band 24 may include a first attachment point adjacent to the palmer surface and second attachment point adjacent to the dorsal surface. When the glove 10 is in the first position 34, the movable tension device 32 attaches to the first attachment point. When the glove 10 is in the second position 36, the movable tension device 32 attaches to the second attachment point.

The glove 10 may include a cover 70 attached to the glove body 11, wherein the cover 70 conceals the tension bands 26 between the glove body 11 and the cover 70. The cover 70 may be the same material as the glove body 11. In an example, the cover 70 is sewn to the glove body around the perimeter of the finger portions 14 and a portion of the palm portion 12. The remaining portion of the cover 70 that is not sewn to the glove body 11 may create a cover opening 84 that may removably connect to the glove body 11 via any suitable cover fastener 86, such as a hook and loop fastening system, snaps, zipper, buttons, among a variety of other fastening mechanisms. As shown in FIGS. 4A-4B, a rigid insert 76 is positioned between an outer surface of the glove body 11 and the cover 70, in order to provide tension to a user's hand during flexion. The glove may also have a cover 70 on the palmer surface 20, such that the rigid insert 76 may be positioned between an outer surface of the palmer surface 20 and the cover 70.

Figure 8A:
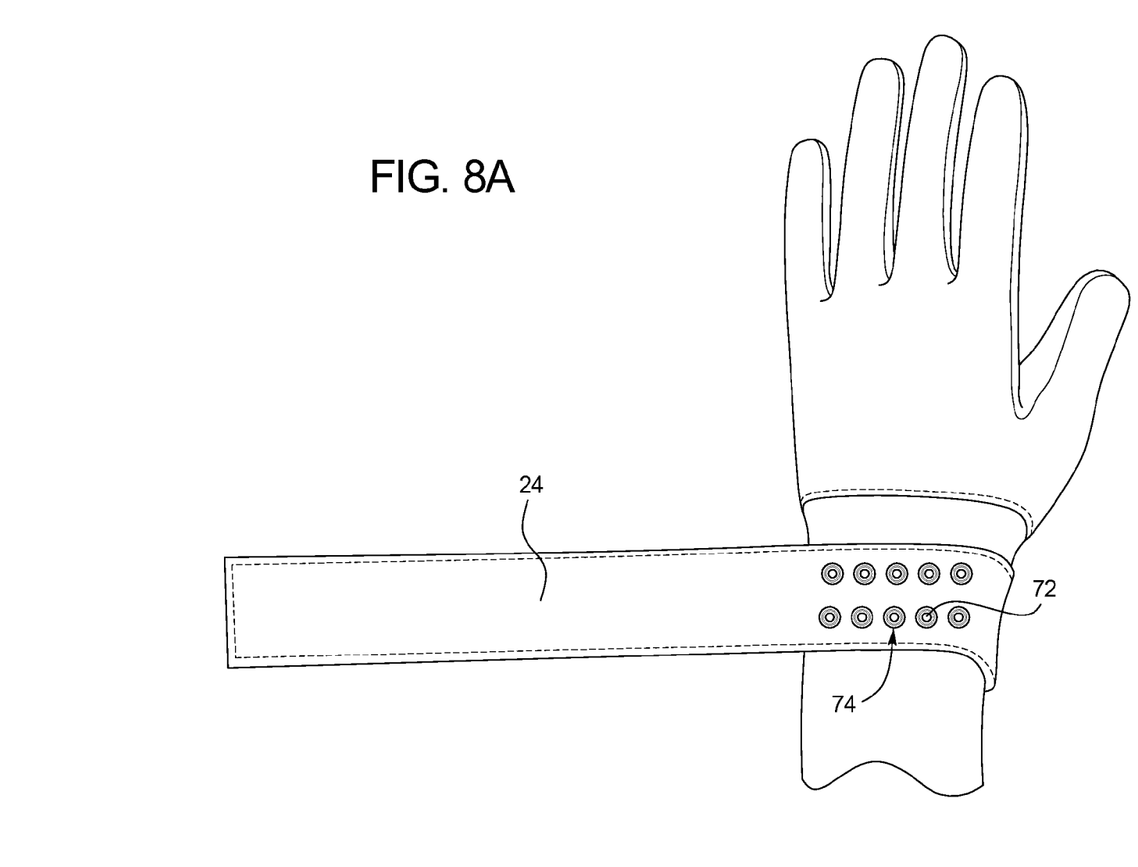
FIGS. 8A-8C are perspective views of an embodiment of the glove disclosed herein including a plurality of connectors.
Figure 8B:
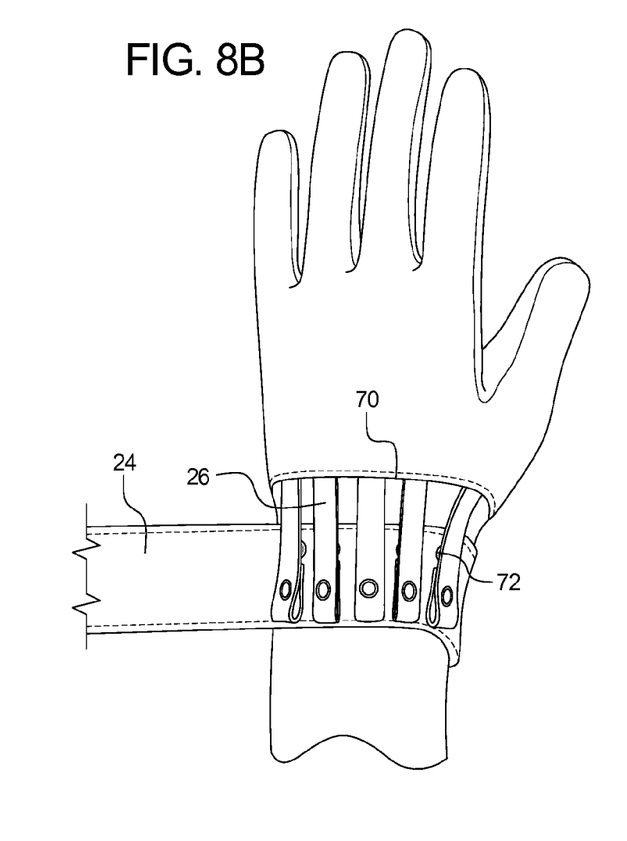
Figure 9:
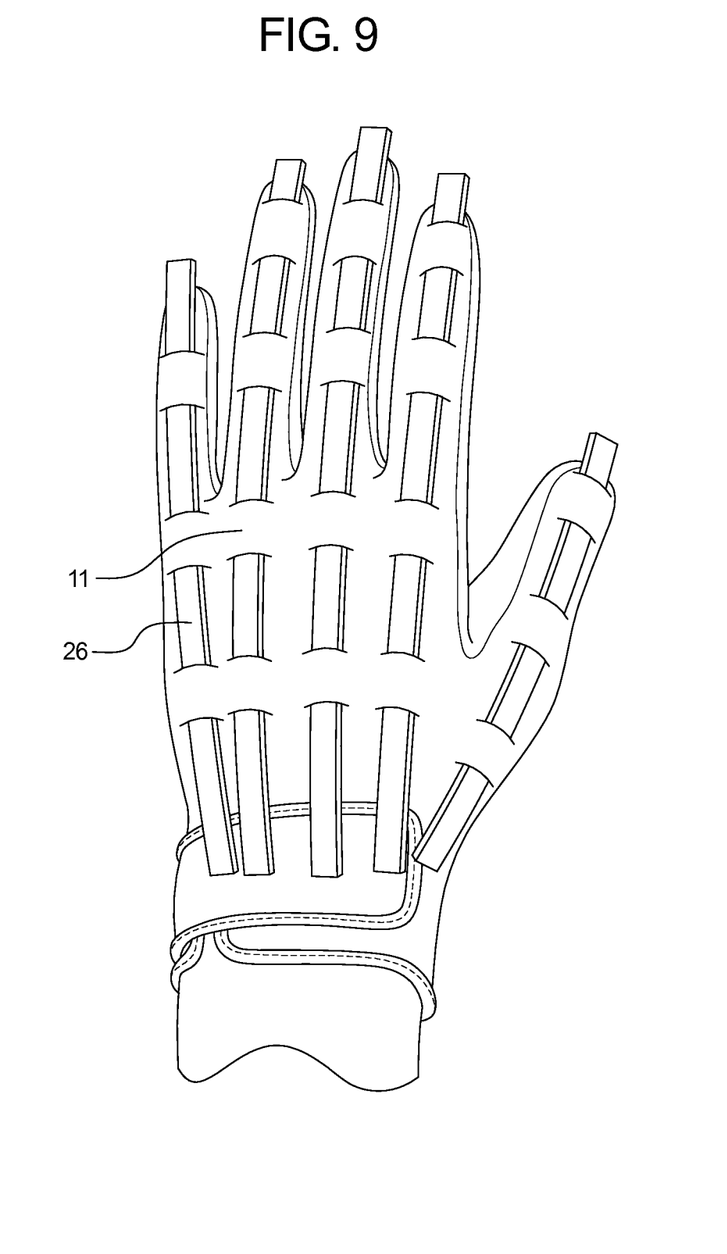
FIG. 9 is a perspective view of an embodiment of the glove wherein the tension bands are interwoven through the glove material.

In yet another example, the movable tension device 32 may include a plurality of connectors 72 attached to the wrist portion 16, wherein the second end 30 of the tension bands 26 removably attach to the connectors 72, as shown in FIGS. 8A-8B and FIG. 9. In an example, the movable tension device 32 may include a set 74 of at least two connectors 72, wherein each tension band 26 corresponds to a set 74 of at least two connectors 72. In such example, the second end 30 of the tension band 26 may be removably attached to the at least two connectors 72.

The connectors 72 within each set 74 may be aligned proximal and distal to each other, such that the user may increase or decrease the tension based on which connector 72 the second end 30 of the tension band 26 is attached. Further, the tension in each tension band 26 may be individually selected, such that not every tension band 26 has the same tension applied. In other words, each finger portion 14 may have a customized tension applied to the finger portion 14 based on which connector 72 within the set 74 of connectors the second end 30 is attached.

Figure 8C:
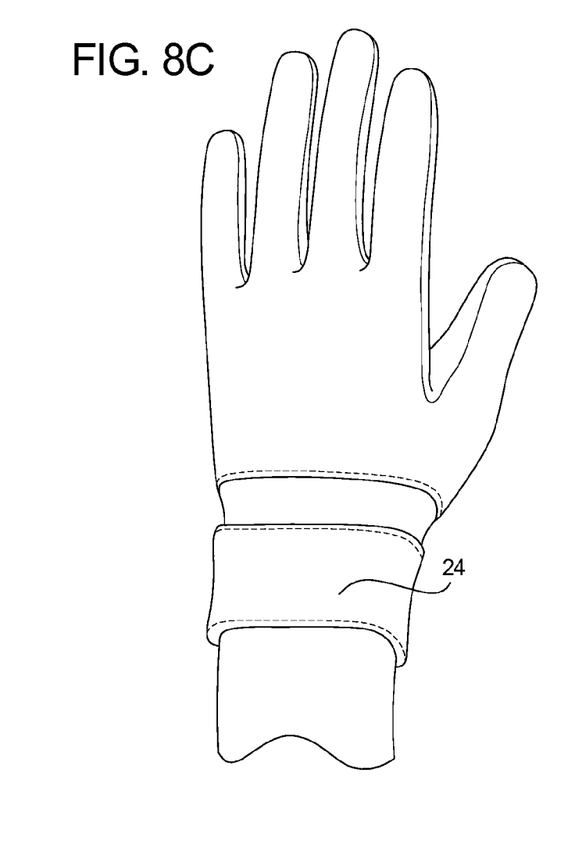

In such example, the tension bands 26 are positioned between the glove body 11 and the cover 70, as shown, for example, in FIG. 8B. The cover 70 is not only aesthetically pleasing, but also is a safety precaution to prevent the tension bands 26 from being caught on various items while the glove 10 is being worn. In addition, as shown in FIG. 8C, the wrist band 24 may cover at least a portion of the movable tension device 32. In another example shown in FIG. 9, the tension bands 26 may be interweaved within the glove body 11.

Figure 5A:
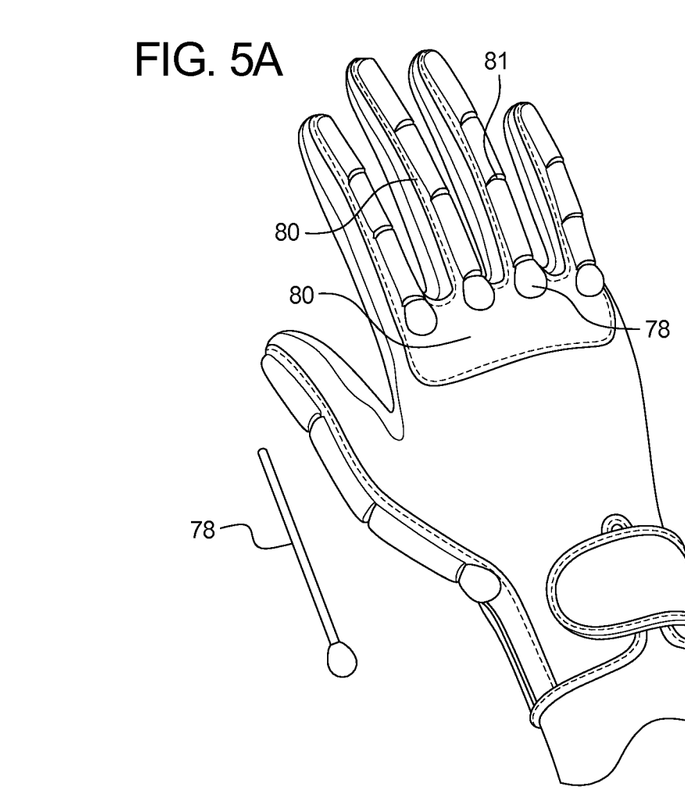
FIGS. 5A-5B are perspective views of an embodiment of the glove including rigid pins.
Figure 5B:
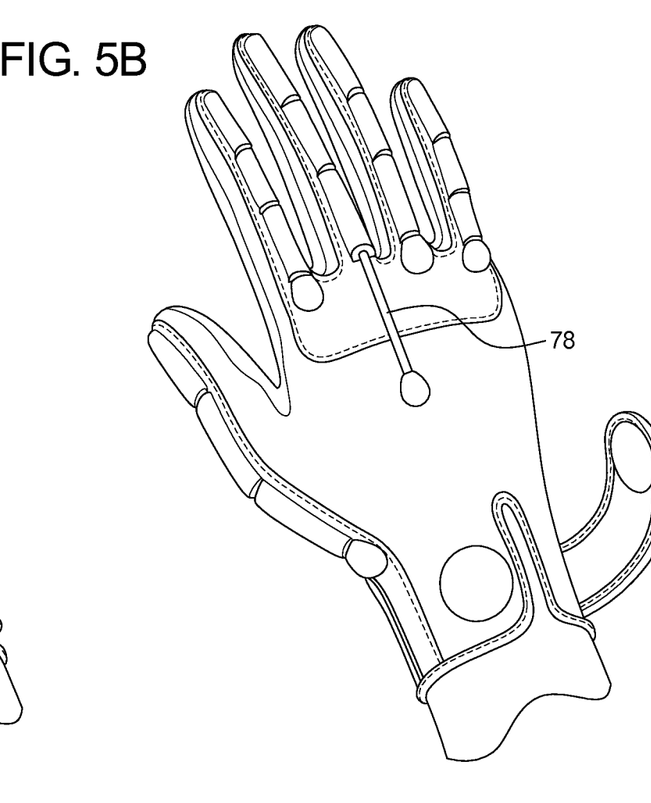

As shown in FIGS. 5A-5B, the glove 10 may include a plurality of tension pins 78 that are positioned within channels 81 of a molded pin receiver 80. Each finger portion 14 may have a corresponding tension pin 78 that may be inserted into the groove 82 of the molded pin receiver 80. The tension pins 78 may all have the same rigidity, or tension pins 78 of differing rigidity may be used according to the specific injury or rehabilitation prescription. For example, if a user's middle finger has not healed as strong as the other fingers, the user may use a less rigid tension pin 78 that the tension pins 78 used in the remaining channels 81 of the finger portions 14. The tension pins 78 may include an easy to grab tear-shaped or spherical knob at the end of the pin that a user may grab to insert and remove the tension pins 78 from the channels 81. Further, the tension pins 78 may be linear or slightly curved.

The molded pin receiver 80 may be made of a more rigid material than that of the glove body 11. For example, the molded pin receiver 80 may be made of flexible plastic, wherein the glove body may be made of neoprene or fabric. As shown in FIGS. 5A-5B, the channels 81 of the molded pin receiver 80 may include three sections corresponding with digits of a user's finger. Alternatively, each channel 81 may be one continuous channel 81 from the knuckle portion of a user's hand to the distal portions 15 of the finger portions 14.

Figure 10:
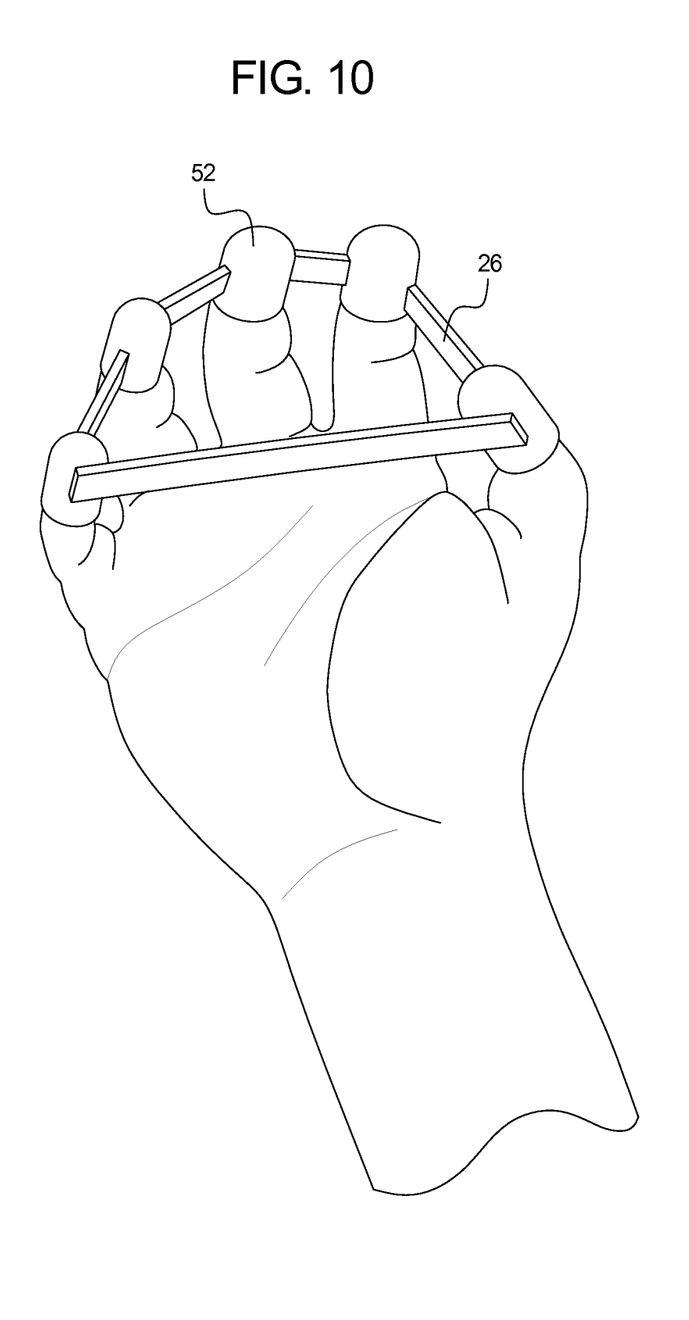
FIG. 10 is a perspective view of an embodiment of the glove wherein the finger portions are connected to each other through a set of tension bands.

In yet another example, shown in FIG. 10, the molded caps 52 of the finger portions 14 are connected to each other through a set of tension bands 26. The molded caps 52 and the interconnected tension bands 26 may be a separate apparatus configured to be used in connection with the various glove 10 embodiments disclosed herein. Alternatively, the glove 10 may include a palm portion 12, five finger portions 14, and a wrist portion 16 including a wrist opening 18 configured to receive a hand of a user, wherein the finger portions 14 include molded caps 52 interconnected by tension bands 26.

It should be noted that various changes and modifications to the embodiments described herein will be apparent to those skilled in the art. Such changes and modifications may be made without departing from the spirit and scope of the present invention and without diminishing its attendant advantages. For example, various embodiments of the method and portable electronic device may be provided based on various combinations of the features and functions from the subject matter provided herein.

I claim:

1. A variable tension rehabilitation glove comprising:
   a glove body comprising a palm portion, five finger portions, and a wrist portion including a wrist opening configured to receive a hand of a user, wherein the glove body includes a palmer surface and a dorsal surface;
   a wrist band surrounding at least a portion of the wrist portion; and
   a plurality of tension bands each including a first end and a second end, wherein the first end is connected to a distal end of the finger portions and the second end is attached to a movable tension device for varying the tension of the tension bands, wherein the movable tension device is connected to the wrist band,
   wherein the glove is convertible between a first position and a second position,
   wherein, when the glove is in the first position, the tension bands extend along the palmer surface of the finger portions and the movable tension device is adjacent to the palmer surface of the palm portion,
   wherein, when the glove is in the second position, the tension bands extend along the dorsal surface of the finger portions and the movable tension device is adjacent to the dorsal surface of the palm portion;
   wherein the first end of the tension bands includes a band opening and the distal portions of the finger portions include a hook, wherein the band opening engages with the hook.

2. The glove of claim 1, wherein the movable tension device includes a longitudinal base plate and a connector plate engaged to slide along at least a portion of the length of the longitudinal base place, wherein the second ends of the tension bands connect to the connector plate, wherein the connector plate may temporarily lock into a plurality of positions along the length of the longitudinal base place, wherein the position of the connector plate relative to the longitudinal base plate effects the tension in the tension bands.

3. The glove of claim 2, wherein, when the glove is in the first position, the longitudinal base plate is adjacent to the palmer surface of the glove body, and wherein, when the glove is in the second position, the longitudinal base plate is adjacent to the dorsal surface of the glove body.

4. The glove of claim 1, wherein the wrist band includes two operative ends configured to releasably attach to each other.

5. The glove of claim 1, wherein the wrist band includes an inner surface and an outer surface, wherein, when the glove is in the first position, the inner surface of the wrist band is adjacent to a wrist of a user, wherein, when the glove is in the second position, the outer surface of the wrist band is adjacent to a wrist of a user.

6. The glove of claim 1, wherein the distal portions of the finger portions include molded caps including finger tip anchorings, wherein the first end of the tension band attaches to the finger tip anchoring.

7. The glove of claim 1, wherein the movable tension device includes a spring-loaded button configured to adjust the tension in the tension bands.

8. The glove of claim 1, wherein the finger portions include a molded band guide that includes a groove to receive the tension band.

9. The glove of claim 1, wherein the movable tension device includes an adjustment knob, wherein rotation of the adjustment knob effects the tension in the tension bands.

10. The glove of claim 1, wherein the movable tension device includes a connector plate connected to a rod including a plurality of rod openings, wherein the wrist band includes a spring-loaded pin connected to a housing, wherein the housing receives at least a portion of the rod, wherein the pin is movable between the plurality of openings in the rod to alter the tension in the tension bands.

11. The glove of claim 1 further comprising a cover attached to the glove body, wherein the cover conceals the tension bands between the glove body and the cover.

12. The glove of claim 1, further comprising a cover for the glove body to conceal the tension bands;

wherein the movable tension device comprises a rigid insert positioned between the cover and an outer surface of the glove body.

13. The glove of claim 12, wherein movement of the rigid insert effects the tension in the tension bands.

14. The glove of claim 1, wherein the movable tension device comprises a plurality of connectors attached to the wrist portion, wherein each of the second end of the tension bands removably attaches to one of the plurality of connectors.

15. A variable tension rehabilitation glove comprising:
a glove body comprising a palm portion, five finger portions, and a wrist portion including a wrist opening configured to receive a hand of a user, wherein the glove body includes a palmer surface and a dorsal surface;
a wrist band surrounding at least a portion of the wrist portion; and
a plurality of tension bands each including a first end and a second end, wherein the first end is connected to a distal portion of the finger portions and the second end is attached to a movable tension device for varying the tension of the tension bands, wherein the movable tension device is connected to the wrist band; and
a cover attached to the glove body, wherein the cover conceals the tension bands between the glove body and the cover;
wherein the movable tension device includes a plurality of connectors attached to the wrist portion, wherein the second end of the tension bands removably attach to the connectors.

16. The glove of claim 15, wherein the movable tension device includes a set of at least two connectors, wherein each tension band corresponds to a set of at least two connectors, wherein the second end of the tension band is removably attached to the at least two connectors.

17. The glove of claim 16, wherein the connectors within each set are aligned proximal and distal to each other.

18. The glove of claim 16, wherein the wrist band covers at least a portion of the movable tension device.

* * * * *